(12) United States Patent
Ley et al.

(10) Patent No.: US 9,468,225 B2
(45) Date of Patent: Oct. 18, 2016

(54) ORAL COMPOSITIONS

(71) Applicant: Symrise AG, Holzminden (DE)

(72) Inventors: Jakob Ley, Holzminden (DE); Sabine Widder, Holzminden (DE); Veronika Somoza, Weidling (AT); Barbara Rohm, Vienna (AT); Matthias Zaunschirm, Lengenfeld (AT); Gerhard Krammer, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/179,170

(22) Filed: Feb. 12, 2014

(65) Prior Publication Data

US 2014/0234412 A1    Aug. 21, 2014

(30) Foreign Application Priority Data

Feb. 16, 2013  (EP) .................................... 13155556

(51) Int. Cl.
*A61K 31/16* (2006.01)
*A61K 31/164* (2006.01)
*A23K 20/105* (2016.01)
*A23K 1/16* (2006.01)
*A23L 1/29* (2006.01)
*A23L 1/30* (2006.01)

(52) U.S. Cl.
CPC ........... *A23K 1/1609* (2013.01); *A23K 20/105* (2016.05); *A23L 1/293* (2013.01); *A23L 1/30* (2013.01); *A61K 31/16* (2013.01); *A61K 31/164* (2013.01)

(58) Field of Classification Search
None
See application file for complete search history.

(56) References Cited

U.S. PATENT DOCUMENTS

| 3,720,762    | A  * | 3/1973  | Iioka et al. ..................... 424/58 |
| 2005/0234132 | A1 * | 10/2005 | Gatfield et al. ............... 514/627 |
| 2008/0050500 | A1 * | 2/2008  | Muranishi et al. ........... 426/590 |
| 2009/0124701 | A1 * | 5/2009  | Langer et al. ................. 514/627 |

FOREIGN PATENT DOCUMENTS

| EP | 1977655 A1 | 10/2008 |
| EP | 2058297 A1 | 5/2009 |
| WO | 2004/043906 A2 | 5/2004 |
| WO | 2011/112067 A1 | 9/2011 |
| WO | WO 2014182791 A1 * | 11/2014 ............. A23L 1/293 |

* cited by examiner

*Primary Examiner* — Carlos Azpuru
*Assistant Examiner* — Casey Hagopian
(74) *Attorney, Agent, or Firm* — Dilworth & Barrese, LLP (57) ABSTRACT

Suggested are new compositions for oral ingestion, comprising at least one active agent from the group of alkamides. The compositions which are orally ingested reduce the uptake of free fatty acids in the adipocytes and at the same time stimulate the release of serotonin and dopamine, which leads to a reduction of appetite, a feeling of satiety and a positive mood. In doing so, the new compositions are thus perfectly suitable to counteract any undesired gain of weight.

5 Claims, 6 Drawing Sheets

Serotonin release following incubation with t-pellitorine in concentrations of 0.001 μM, 0.1 μM, 1 μM and 10 μM.

Figure 1A

Serotonin release following incubation with t-pellitorine in concentrations of 0.001 µM, 0.1 µM, 1 µM and 10 µM.

Figure 1B

Serotonin release following incubation with other alkamides in concentrations of 0.001 μM, 0.1 μM, 1 μM and 10 μM, (1 = t-pellitorine, 2 = dihydropellitorine, 3 = spilanthol).

Figure 2

Dopamine release after incubation with t-pellitorine (2) in concentrations of 0.001 µM, 0.1 µM, 1 µM and 10 µM.

Figure 3

Fatty acid uptake after a preincubation of 30 minutes with different concentrations of trans-pellitorine in concentrations of 0.1 µM, 1 µM and 10 µM

Figure 4

Lipid accumulation after incubation with different concentrations of trans-pellitorine (2) in concentrations of 0.001 µM, 0.1 µM, 1 µM and 10 µM. The results are represented in % in comparison to control (1, buffer 0.1% ethanol). n=3, tR=1-4.

Figure 5

Fatty acid uptake after a preincubation of 30 minutes with different concentrations of trans-pellitorine (2) in concentrations of 0.1 µM, 1 µM, 10 µM and 100 µM

ORAL COMPOSITIONS

FIELD OF THE INVENTION

The invention is in the field of food and dietary supplements and relates to a composition with a content of at least one alkamide to counteract overweight and its associated negative physical and mental factors.

PRIOR ART

The frequent occurrence of a permanently overweight condition caused by lack of exercise and/or too much food ingestion may lead to chronic diseases such as adipositas, insulin resistance, lipid metabolism disorders and/or high blood pressure, while the serious secondary disorders—type II diabetes, arteriosclerosis, myocardial or cerebral infarction—may in a last consequence lead to an early death. It is particularly the high content of easily metabolizable carbohydrates, proteins and, above all, fats in our diet that leads to the formation of fat depots, which may, eventually, severely contribute to the above-mentioned problems. In order to restrict the ingestion of these hedonically often very preferred food constituents, particularly, of the fats and sweet carbohydrates (sugar), the content of those is often severely reduced in low-calorie foods, which are referred to as "low-fat products", and exchanged for substitute substances (thickeners instead of fats, calorie-free sweeteners instead of the sugars).

When consuming "low-fat products", it may frequently happen that a product—thanks to clever formulation—which possesses a hedonic value comparable to the one of the high-energy original product is consumed in larger amounts, and as a result an increased ingestion of calorically relevant food constituents may occur, thus missing the aim of reducing the ingested calorie amount.

To counteract an increased ingestion of calorically relevant food constituents, it has been desired for quite a long time to find food constituents, particularly such that have already been evaluated as safe, approved for use in food and generally accepted flavouring substances, which may reduce both the sensation of feeling hungry and the natural appetite and/or are capable of increasing the feeling of satiety accordingly. It is known that appetite may be influenced negatively, and satiety positively, by increasing the release of dopamine and serotonin in certain brain areas with a simultaneous exposition to nutrients by the orally consumable products (particularly food) as well as by inducing leptin receptor proteins and serotonin receptor proteins.

Besides having an effect on both appetite and satiety, also the mood of the consumer may be positively influenced. For example, foods are known which comprise dopamine and serotonin and which possess a mood-enhancing effect. Provided that serotonin is present in the brain in sufficient amounts, it conveys a positive mood, provides power of concentration and optimism. Lower serotonin levels, however, may lead to irritability, sleep disorders, lack of power of concentration and depression. Dopamine influences alertness, happiness and lucidity. Lack of dopamine shows, for example, in apathy, lack of empathy and lack of remorse.

Ingesting serotonin and dopamine via food increases the serotonin or dopamine concentrations in the blood, and with some probability are available for interaction with brain receptors. To increase the serotonin or dopamine concentration in the brain it is advantageous to stimulate the release of serotonin or dopamine in the brain.

The ingestion of calorically relevant food constituents is more directly counteracted by reducing their adsorption, because this would, for example, affect the body's own reserves to a larger degree such that, eventually, not only the body's own fat reservoirs are broken down but, in addition, the number of adipocytes is at least not increased. In this context it is particularly helpful to counteract the absorption of long-chain free fatty acids (FFA) or their long-time accumulation in adipocytes as triglycerides. Thus a reduction of the absorption of fatty acids in the small intestine—as it has already been shown for lipase inhibitors such as Olestra® with a simultaneous increase of the breakdown of endogeneous fat reserves—might contribute to achieving and maintaining a healthy body weight and prevent the formation of adipositas.

The complex object on which the present invention is based has thus been to find a flavouring substance which is, preferably, approved for use in food products or a plant extract containing said flavouring substance, which at the same time
Reduces appetite
Conveys a feeling of satiety when consuming it and
Enhances the mood and, in sum,
Reduces the energy intake.

DESCRIPTION OF THE INVENTION

In a first form of embodiment the subject matter of the invention concerns an oral composition comprising at least one alkamide selected from the group consisting of 2E,4E-decadienic acid-N-isobutylamide (trans-pellitorine); 2E,4Z-decadienic acid-N-isobutylamide (cis-pellitorine); 2Z,4Z-decadienic acid-N-isobutylamide; 2Z,4E-decadienic acid-N-isobutylamide, 2E,4E-decadienic acid-N-([2S]-2-methylbutyl)amide; 2E,4E-decadienic acid-N-([2S]-2-methylbutyl)amide; 2E,4E-decadienic acid-N-([2R]-2-methylbutylamide); 2E,4Z-decadienic acid-N-(2-methylbutyl)amide; 2E,4E-decadienic acid-N-piperidine (achilleamide); 2E-decenoic acid-N-isobutylamide; 2E,6Z,8E-decatrienoic acid N-isobutylamide (spilanthol); 2E,6Z,8E-decatrienoic acid N-([2S]-2-methylbutyl)amide (homospilanthol); 2E,6Z,8E-decatrienoic acid-N-([2R]-2-methylbutyl)amide; 2E-decen-4-inoic acid-N-isobutyl amide; 2Z-decen-4-inoic acid N-isobutyl amine; 2E,6Z,8E,10E-dodecatetraenoic acid N-(2-methylpropyl)amide (α-sanshool); 2E,6Z,8E,10E-dodecatetraenoic acid N-(2-hydroxy-2-methylpropyl)amide (α-hydroxysanshool); 2E,6E,8E,10E-dodecatetraenoic acid N-(2-hydroxy-2-methylpropyl)amide (β-hydroxysanshool; 2E,4E,8Z,10E,12E-tetradecapentaenoic acid N-(2-hydroxy-2-methylpropyl)amide (γ-hydroxysanshool); 2E,4E,8E,10E,12E-tetradecapentaenoic acid N-(2-hydroxy-2-methylprypyl)amide (γ-hydroxyisosanshool); 2E,4E,8Z,10E,12E-tetradecapentaenoic acid N-(2-methyl-2-propenyl)amide (y-dehydrosanshool); 2E,4E,8Z,10E,12E-tetradecapentaenoic acid N-(2-methylpropyl)amide (y-sanshool); 2E,4E,8Z,11Z-tetradecatetraenoic acid N-(2-hydroxy-2-methylpropyl)amide (bungeanool), 2E,4E,8Z,11E-tetradecatetraenoic acid N-(2-hydroxy-2-methylpropyl)amide (isobungeanool), 2E,4E,8Z-tetradecatrienoic acid N-(2-hydroxy-2-methylpropyl)amide (dihydrobungeanool) and 2E,4E-tetradecadienoic acid N-(2-hydroxy-2-methylpropyl)amide (tetrahydrobungeanool);

Surprisingly it was found that the alkamides according to the invention are already capable of simultaneously
stimulating serotonin release in neurons by a maximum of up to ca. 170% in comparison with the respective control in a range of concentration of from 0.001 µM to 1 µM (ca. 0.002 mg/kg to ca. 0.2 mg/kg)

stimulating dopamine release following acetylcholine stimulation by up to ca. 170% in comparison with the respective control in a concentration of about 0.1 µM (ca. 0.2 mg/kg);

decreasing the uptake of free fatty acids in adipocytes by between 5 and 10% in comparison with the respective control in a concentration of between 0.01 and 10 µM (ca. 0.02 mg/kg to ca. 2 mg/kg); and decreasing long-time accumulation of triglycerides in adipocytes by between 5 and 7% in comparison with the respective control in a concentration of between 0.001 and 1 µM (ca. 0.002 mg/kg to ca. 0.2 mg/kg).

BRIEF DESCRIPTION OF THE DRAWINGS

The present invention will be described in greater detail with reference to the accompanying drawings in which.

DESCRIPTION OF THE PREFERRED EMBODIMENTS

The preferred alkamides contained in the compositions are pellitorines and/or spilanthol.

The respective concentrations of alkamides are too low in comparison with typically used concentrations to achieve a flavour effect, and it is, therefore, not likely that strongly perceivable tingling effects will occur.

Alkamides

The alkamides to be used according to the invention in the following are particularly selected from the group consisting of 2E,4E-decadienic acid-N-isobutylamide (trans-pellitorine); 2E,4Z-decadienic acid-N-isobutylamide (cis-pellitorine); 2E,4E-decadienic acid-N-piperidine (achilleamide); 2E-decenoic acid-N-isobutylamide; 2E,6Z,8E-decatrienoic acid N-isobutylamide (spilanthol); 2E,4E-dodecenoic acid-N-isobutylamide and 2E,4E-tetradecenoic acid-N-isobutylamide.

Particularly preferred are the following alkamides to be used according to the invention selected from the group consisting of 2E,4E-decadienic acid-N-isobutylamide (trans-pellitorine, formula 1), 2E-decenoic acid-N-isobutylamide (formula 2) and 2E,6Z,8E-decatrienoic acid N-isobutylamide (spilanthol), formula 3)).

The following figure shows the compounds of formulae (1), (2) and (3) for reasons of greater clarity:

Alkamides, particularly 2E,4E-decadienic acid-N-isobutylamide (trans-pellitorine), 2E-decenoic acid-N-isobutylamide and 2E,6Z,8E-decatrienoic acid N-isobutylamide (spilanthol) are known flavouring substances. They are predominantly used to obtain a sensoric tingling effect (Bryant, B. P.; Mezine, I., Alkylamides that produce tingling paresthesia activate tactile and thermal trigeminal neurons. Brain Res. 1999, 842, 452-460), but also to increase salivation (for example, as described in EP 1,562,893-B1 or in WO 2005 044,778) as well as to mask unpleasant taste impressions (for example, as described in EP 2,058,297 or EP 2,008,530-B1).

WO 2011 112,067 A1 describes a plant extract (Nobesiti) from *Piper sarmentosum* as a means to counteract overweight conditions, wherein the extract comprises—besides rutin, flavonone, sarmentine, sarmentosine, polyphenols, further amides and glycosaponins—also pellitorine.

Natural sources, preferably plant extracts, are known to provide alkamides, which are suitable within the meaning of the invention. Particularly suitable for preferred alkamides are plant extracts such as, for example, alkamide-containing pepper extract (*Piper* ssp., especially *P. nigrum*, *P. hispidum*, *P. tuberculatum*, *P. longum*, *P. arboreum*, *P. futokadsura*, *P. guineense* or *Piper nigrum*, Var. *muntok*, P. aff. *Pedicellatum*), extracts of "toothache grass", *Ctenium aromaticum*), extracts of tarragon (*Artemisia dracunculus*), extracts of Spanish chamomile root (*Anacyclus* ssp., especially *Anacyclus pyrethrum* L.), Echinacea extracts (*Echinaceae* ssp., e.g., *E. angustifolia*), exctracts from Szechuan pepper (*Zanthoxylum* ssp., especially *Zanthoxylum piperitum*, *Z. clavaherculin*, *Z. bungeanum*, *Z. zanthoxyloides*), extracts of *spilanthes* or paracress (*Spilanthes* ssp., especially *Spilanthes acmella*), extracts of *Acmella* ssp. (e.g. *A. ciliata*), extracts of *Achillea* ssp. (e.g., *Achillea wilsoniana*), extracts of *Fagara* species (*Fagara zanthoxyloides*), extracts of *Heliopsis* ssp. (e.g. *H. longipes*), extracts of *Cissampelos glaberrima*, extracts of *Dinosperma erythrococca*, extracts of the bark of *Esenbeckia alata* and extracts of *Stauranthus perforatus*.

The plant extracts containing one or more of the alkamides can be obtained from the respective fresh or dried plants or plant parts, particularly, from white, green or black pepper corns (*P. nigrum*), Long pepper (*P. longum*), Echinacea root, Spanish chamomile root, Szechuan pepper, parts of the other *Zanthoxylum* species, plant parts of the *Spilanthes* or *Acmella* species, plant parts of the *Fagara* or *Heliopsis* species. The dried plant parts (e.g. fresh or dried roots, fruit, seeds, peel, wood, stems, leaves or [parts of] flowers), usually present in a preferably shredded form, are extracted with a solvent suitable for food and products consumed for pleasure at temperatures of between 0° C. and the boiling point of the respective solvent or solvent mixture, subsequently filtered, and the filtrate fully or partly concentrated, preferably, by distillation, freeze- or spray drying. The raw extract obtained in this way can then be further processed, for example by enzymatic treatment, with acid (e.g. under pressure), treated with acid ion exchangers or with steam, usually at pressures of between 0.01 mbar and 100 bar, preferably at between 1 mbar and 20 bar, and/or included in a solvent suitable for food and products consumed for pleasure. Particularly preferred are extracts having a major part of alkamides, particularly 2E,4E-decadienic acid-N-isobutylamide (trans-pellitorine), 2E-decenoic acid-N-isobutylamide and 2E,6Z,8E-decatrienoic acid N-isobutylamide (spilanthol) based on the total amount of amide-type compounds, preferably 10% by weight, more preferably 20% by weight, more preferably 50% by weight, particularly preferably 80% by weight based on the total amount of amide-type compounds.

Solvents used for extraction that are particularly suitable for food and products consumed for pleasure are water, ethanol, methanol, 1,2-propylene glycol, glycerol, acetone, dichloromethane, acetic acid ethyl ester, diethyl ether, hexane, heptane, triacetine, vegetable oils or fats, supercritical carbon dioxide and mixtures thereof.

The alkamides can be confectioned together with additives and carriers. Preferred for this purpose are maltodextrin, starch, natural or synthetic polysaccharides and/or vegetable gums such as modified starch or gum arabic, solvents approved for use in flavouring compositions such as, for example, ethanol, 1,2-propylene glycol, water, glycerol, triacetine, vegetable triglycerides, colourants, for example, food colourants approved for use in food, colouring plant extracts, stabilisers, preservatives, antioxidants and viscosity modifiers.

Compositions Intended for Oral Ingestion

The compositions within the meaning of the present invention may be food, feed or, particularly, dietary supplements comprising the alkamides—based on the total weight of the orally consumable product in amounts of 2 mg/kg or less, preferably, in a concentration of 0.20 mg/kg or less, particularly preferably in a concentration of 0.10 mg/kg or less.

Preferably, the alkamides based on the total weight of the orally consumable product are present in a concentration of at least 0.0001 mg/kg or more, more preferably in a concentration of 0.001 mg/kg or more, and particularly preferably in a concentration of 0.005 mg/kg or more.

Preferred is an orally consumable product according to the invention, which is a liquid or a solid composition including a semi-finished product.

Within the scope of the present text, the term "food" comprises a multitude of products. The term "food" covers, in particular, products as discussed below in context with food according to the invention. The term, in particular, comprises products which are food according to the REGULATION (EC) No. 178/2002 OF THE EUROPEAN PARLIAMENT AND OF THE COUNCIL of 28 Jan. 2002. Pursuant to said regulation "food" means all substances or products intended to, or of which it may be expected according to reasonably practicable measures, that they may be ingested by humans in a processed, partly processed, or unprocessed state. "Food" also includes beverages, chewing gum and all substances—including water—which are purposefully added to the food during its production or further processing.

The term "feed" comprises, within the scope of the present text, all forms of animal feed. A multitude of the food stated below may also be used as feed.

It is clear that food or feed may be transformed to corresponding pharmaceutical products by adding substances or substance compositions which, as means, have properties intended to heal or prevent human or animal diseases.

Spray-Dried Formulations

Particularly when the compositions according to the invention concern dietary supplements, these are preferably spray-dried substances, comprising constituents suitable for consumption, solid carrier substances and, optionally, particular flavouring substances or flavouring compositions. It is understood that said additives need to be suitable for consumption.

Preferred carrier substances in said preferred, preferably spray-dried, substance mixtures according to the invention are, preferably, silicon dioxide (silicic acid, silica gel), carbohydrates and/or carbohydrate polymers (polysaccharides), cyclodextrins, starches, starch hydrolysates, chemically or physically modified starches, modified celluloses, gum arabic, ghatti gum, traganth, karaya, carrageenan, guar, locust bean, alginates, pectin, inulin, or xanthan gum. Preferred starch hydrolysates are maltodextrins and dextrins.

Preferred carrier substances are silicon dioxide, gum arabic and maltodextrins, whereby maltodextrins with DE values in the range of between 5 and 20 are preferred. Here it is insignificant what plant originally supplied the starch used for the production of the starch hydrolysates. Suitable and easily accessible are maize-based starches as well as starches from tapioca, rice, wheat or potatoes. The carrier materials can here also function as flow additives such as, for example, silicon dioxide.

The substance mixtures according to the invention which comprise, besides the alkamide or a plurality of alkamides, one or more solid carrier substances which can be produced, for example, by mechanical mixing processes wherein the simultaneous shredding of the particles may be performed, or by means of spray-drying. Preferred are compositions according to the invention, which comprise solid carrier materials and which are manufactured by means of spray-drying; it is referred to U.S. Pat. No. 3,159,585, U.S. Pat. No. 3,971,852, U.S. Pat. No. 4,532,145 or U.S. Pat. No. 5,124,162 with regard to spray-drying.

Preferred substance mixtures according to the invention comprising carrier materials manufactured by means of spray-drying have an average particle size within the range of between 30 and 300 μm and a residual moisture of less or equal than 5% by weight.

A further subject matter of the invention, therefore, relates to a substance mixture, comprising
(a) an effective amount of one alkamide or a plurality of alkamides,
(b) at least one solid carrier material and, optionally,
(c) at least one flavouring substance.

The optional flavouring substance forming component (c) here is preferably a sensorily effective component and preferably used in a concentration larger than its stimulus threshold. Examples for suitable flavouring substances within this meaning are available, for example, in H. Surburg, J. Panten, Common Fragrance and Flavor Materials, 5th. Ed., Wiley-VCH, Weinheim 2006. The flavouring substances can be used in the form of flavouring compositions, which again can be used in the form of thermal process flavourings (Maillard products) and/or extracts or etheric oils from plants or plant parts or fractions thereof.

Encapsulated Formulations

The compositions, particularly when they are dietary supplements, may also be present in encapsulated form, i.e. as macrocapsules or microcapsules.

Typical macrocapsules are obtained by inclusion of the active principles, optionally in a liquid phase, in proteins such as, particularly, gelatin, and have a diameter in the range of from about 0.5 to 1 cm.

"Microcapsules" are understood by the expert to be spherical aggregates with a diameter of about 0.0001 to about 5 mm, which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, molten waxes are absorbed in a matrix ("microsponge") which, as microparticles, may be additionally coated with film-forming polymers. According to a third process, particles are alternatingly coated with polyelectrolytes of different charges ("layer-by-layer" method). The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters.

Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicerin C30 (lactose, microcrystalline cellulose, hydroxypropylnnethyl cellulose), Kobo Glycospheres (modified starch, fatty acid esters, phospholipids), Softspheres (modified agar agar), Kuhs Probiol Nanospheres (phospholipids), Primaspheres and Primasponges (chitosan, alginates) and Primasys (phospholipids).

Food Products

To support the reduction of consumers' body weight it has proven useful to restrict the potential caloric intake. This can be performed, on the one hand, by using the alkamide or a mixture of alkamides according to the invention in orally consumable products (particularly food, feed and pharmaceutical products) which conveys a feeling of satiety and reducing, at the same time, one's appetite, and in addition reduces the absorption of energy-supplying nutrients from the intestine. In doing so, the consumer is not only induced to reduce his consumption of energy-containing products but he will have available less food energy due to a reduced absorption of the orally ingested amount of energy. The intake of calories may additionally be reduced—besides the lower intake caused by the alkamides and accumulation of lipids—by offering orally consumable products according to the invention (particularly food, feed or pharmaceutical products) for consumption which themselves already have a low energy density.

A preferred orally consumable product according to the invention does not contain more than 200 kcal/100 g of the orally consumable product, preferably, not more than 100 kcal/100 g, particularly preferably not more than 40 kcal/100 g.

Preferred orally consumable products according to the invention are any preparations or compositions suitable for consumption, for nutrition, for oral hygiene or for pleasure and are regularly products intended to be introduced into the human or animal oral cavity, to remain there for a certain period of time and then to either be swallowed (e.g., food or feed ready for consumption, see further below) or to be removed from the oral cavity again (e.g. chewing gums or products of oral hygiene or medical mouth washes). These products include all substances or products intended to be ingested by humans or animals in a processed, semi-processed or unprocessed state. This also includes substances which are added to orally consumable products (particularly food, feed and pharmaceutical products) during their production, treatment or processing and intended to be introduced into the human or animal oral cavity.

The orally consumable products according to the invention also include substances intended to be swallowed by humans or animals and then digested in an unmodified, prepared or processed state; the orally consumable products according to the invention therefor also include casings, coatings or other encapsulations which are intended also to be swallowed together with the product or for which swallowing is to be anticipated. The term "orally consumable product" comprises food ready for consumption or feed ready for consumption and should here be understood to mean food or feed which is already fully assembled with regard to the substances which decide taste. The phrase "food ready for consumption" or "feed ready for consumption" also covers corresponding beverages and solid or semisolid food, or feed, ready for consumption. Examples, which may be mentioned, are deep-frozen products, which have to be thawed prior to consumption and heated to consumption temperature. Products such as yogurt or ice cream and also chewing gum or hard caramels count as food, or feed, ready for consumption Preferred orally consumable products according to the invention also comprise "semi-finished products". A semi-finished product in the context of the present text is understood to be an orally consumable product which is unsuitable for use as an orally consumable product ready for consumption (particularly food or feed) due to a very high content in flavouring substances. The semi-finished product is transferred into an orally consumable product ready for consumption (particularly food or feed) only by admixture of at least one further constituent (i.e. by reducing the concentration of the respective flavouring substances) and optionally further process steps (e.g. heating, freezing). Examples of semi-finished products are packet soups, baking flavourings and custard powders.

The orally consumable products according to the invention also include "products for oral care". A product for oral care (also referred to as oral hygiene product or oral hygiene preparation) within the meaning of the invention is understood to be a formulation known to those skilled in the art intended for the cleaning and care of the oral cavity and the throat as well as for refreshing one's breath. This expressly includes the care of teeth and gums. Pharmaceutical forms of conventional formulations for oral hygiene are particularly creams, gels, pastes, foams, emulsions, suspensions, aerosols, sprays, and also capsules, granules, pastilles, tablets, lozenges or chewing gums without that this list is understood to be limiting for the purposes of this invention.

A. Food Compositions

Preferably, the orally consumable product according to the invention comprises one or more compositions intended for nutrition or pleasure. These particularly include (low-calorie) baking products (e.g. bread, dry biscuits, cake, other pastry), sweets (e.g. chocolates, chocolate bar products, other bar products, fruit gum, coated tablets, hard caramels, toffees and caramels, chewing gum), non-alcoholic beverages (e.g. cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, fruit or vegetable juice preparations), instant beverages (e.g. instant cocoa beverages, instant tea beverages, instant coffee beverages), meat products (e.g. ham, fresh sausage preparations or raw sausage preparations, seasoned oder marinated fresh meat or salted meat products), eggs or egg products (dried whole egg, egg white, egg yolk), cereal products (e.g. breakfast cereals, muesli bars, pre-cooked instant rice products), dairy products (e.g. whole fat or fat reduced or fat-free milk beverages, rice pudding, yoghurt, kefir, cream cheese, soft cheese, hard cheese, dried milk powder, whey, butter, buttermilk, partly or wholly hydrolized products containing milk proteins), products from soy protein or other soy bean fractions (e.g. soy milk and products prepared thereof, beverages containing isolated or enzymatically treated soy protein, soy flour containing beverages, preparations containing soy lecithine, fermented products such as tofu or tempe products prepared thereof and mixtures with fruit preparations and, optionally, flavouring substances), fruit preparations (e.g. jams, fruit ice cream, fruit sauces, fruit fillings), vegetable preparations (e.g. ketchup, sauces, dried vegetables, deep-freeze vegetables, pre-cooked vegetables, boiled vegetables), snack articles (e.g. baked or fried potato chips (crisps) or potato dough products, extrudates on the basis of maize or peanuts), products on the basis of fat and oil or emulsions thereof (e.g. mayonnaise, remoulade, dressings, each whole fat or fat-reduced), other ready-made meals and soups (e.g. dry soups, instant soups, pre-cooked soups), seasonings and, particularly, sprinkle-on seasonings, which are used, for example, on snacks, sweetener compositions, sweetener tablets or sweetener sachets, other preparations for sweetening or whitening beverages or of other food. The compositions within the meaning of the invention may also serve as semi-finished products for the production of other compositions intended for nutrition or pleasure. The composition within the meaning of the invention can also be present in the form of capsules, tablets (uncoated and coated tablets, e.g. gastro-resistant coatings), coated tablets, granules, pellets, solid-substance mixtures, dispersions in liquid phases, as emulsions, powders, solutions, pastes or other swallowable or chewable preparations and as a dietary supplement.

B. Low-Calorie or Calorie-Free Sweets

Particularly preferred are low-calorie sweets (e.g. muesli bar products, fruit gum, hard caramels, toffees and caramels, chewing gum), non-alcoholic beverages (e.g. cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, fruit or vegetable juice preparations), instant beverages (e.g. instant cocoa beverages, instant tea beverages), cereal products (e.g. breakfast cereals, muesli bars, pre-cooked instant rice products), dairy products, (e.g. whole fat or fat reduced or fat-free milk beverages, rice pudding, yoghurt, kefir, dried milk powder, whey, buttermilk, partly or wholly hydrolized products containing milk proteins), products from soy protein or other soy bean fractions (e.g. soy milk and products prepared thereof, beverages containing isolated or enzymatically treated soy protein, soy flour containing beverages, preparations containing soy lecithine, fermented products such as tofu or tempe products prepared thereof and mixtures with fruit preparations and, optionally, flavouring substances), sweetener compositions, sweetener tablets or sweetener sachets, other preparations for sweetening or whitening beverages or of other food.

Particularly preferred are low-calorie or calorie-free sweets (e.g. muesli bar products, fruit gum, coated tablets, hard caramels, toffees and caramels, chewing gum), non-alcoholic beverages (e.g., green tea, black tea, black or green tea beverages enriched with extracts of green or black tea, Rooibos tea, other herbal teas, fruit-containing low-sugar or sugar-free lemonades, isotonic beverages, nectars, fruit and vegetable juices, fruit or vegetable juice preparations), instant beverages (e.g., instant green tea, black tea, Roibos tea, herbal tea beverages), cereal products (e.g. low-sugar or sugar-free breakfast cereals, muesli bars), dairy products, (e.g. fat reduced or fat-free milk beverages, yoghurt, kefir, whey, buttermilk), products from soy protein or other soy bean fractions (e.g. soy milk and products prepared thereof, beverages containing isolated or enzymatically treated soy protein, soy flour containing beverages, preparations containing soy lecithine or products made thereof and mixtures with fruit preparations and, optionally, flavouring substances) oder sweetener compositions, sweetener tablets or sweetener sachets.

The compositions can also be present as capsules, tablets (uncoated and coated tablets, e.g. gastro-resistant coatings), coated tablets, granules, pellets, solid-substance mixtures, dispersions in liquid phases, as emulsions, powders, solutions, pastes or other swallowable or chewable preparations and as a dietary supplement.

The semi-finished products usually serve the purpose of producing preparations that are ready to use or ready to eat intended for nutrition or pleasure.

C. Auxiliaries and Additives

Further constituents of a consumable composition or semi-finished product intended for nutrition or pleasure can be conventional raw materials, auxiliaries and additives for food and beverages, e.g., water, mixtures of fresh or processed plant-based or animal-based raw or basic materials (e.g. crude, fried, dried, smoked and/or boiled meat, bones, cartilage, fish, vegetables, herbs, nuts, vegetable juices or vegetable pastes or the mixtures thereof), digestible or non-digestible carbohydrates (e.g. saccharose, maltose, fructose, glucose, dextrins, amylose, amylopektin, inulin, xylans, cellulose, tagatose), sugar alcohols (e.g. sorbitol, erythritol), natural or hydrogenated fats (e.g., tallow, lard, palm fat, coconut fat, hydrogenated vegetable fat), oils (e.g., sunflower oil, peanut oil, maize germ oil, olive oil, fish oil, soybean oil, sesame oil), fatty acids or salts thereof (e.g., potassium stearate), proteinogenic or non-proteinogenic amino acids and related compounds (e.g., γ-aminobutric acid, taurine), peptides (e.g., glutathione), native or processed proteins (e.g., gelatin), enzymes (e.g., peptidases), nucleic acids, nucleotides, flavour correctants to correct unpleasant taste, other taste modulators for other, usually not unpleasant tastes, other taste modulating substances (e.g., inositol phosphate, nucleotides such as guanosin monophosphate, adenosine monophosphate or other substances such as sodium glutamate or 2-phenoxypropionic acid), emulsifiers (e.g., lecithins, diacylglycerols, gum arabic), stabilizers (e.g., carrageenan, alginate), preservatives (e.g., benzoic acid and the salts thereof, sorbic acid and the salts thereof), antioxidants (e.g., Tocopherol, ascorbic acid), chelators (e.g. citric acid), organic or inorganic acidifers (e.g., acetic acid, phosphoric acid), additional bitter principles (e.g., quinine, caffeine, limonin, amarogentin, humolones, lupolones, catechins, tannins), substances inhibiting enzymatic browning (e.g., sulfite, ascorbic acid), etheric oils, plant extracts, natural or synthetic colourings or colour pigments (e.g., carotinoids, flavonoids, anthocyanins, chlorophyll and the derivatives thereof), seasonings, substances affecting the trigeminal nerve or plant extracts containing substances affecting the trigeminal nerve, synthetic, natural or nature-identical flavouring substances or fragrances and odour correcting agents.

Preferably, orally consumable products according to the invention contain (particularly food, feed and pharmaceutical products), e.g., in the form of compositions or semi-finished products a flavouring composition to top off and refine their taste and/or odour. A composition may comprise as constituents a solid carrier substance and a flavouring composition. Suitable flavouring compositions contain, e.g., synthetic, natural or nature-identical flavouring substances, odorous substances and taste-producing substances, thermal process flavourings, liquid smoke or other flavour-providing compositions (e.g., (partial) hydrolysates of protein, preferably, (partial hydrolysates of protein with a high arginin content, grill-like flavourings, plant extracts, seasoning compositions, vegetables and/or vegetable compositions) as well as suitable additives and carrier substances. To this end, particularly suitable are such flavouring compositions or constituents thereof that may cause a roasty, umami (particularly chicken, fish, sea food, beef, pork, lamb, mutton, goat), vegetably (particularly tomato, onion, garlic, celery, leeks, mushrooms, eggplant, seaweed), savoury (particularly black and white pepper, cardamom, nutmeg, pimento, mustard and mustard products), roasted, yeasty, boiled, lardy, salty and/or hot flavour impression thus intensifying the savoury impression. Usually, the flavouring compositions contain more than one of the ingredients mentioned.

The energy density of an orally consumable product (particularly food, feed or pharmaceutical products) can be reduced by substituting high-energy ingredients of the orally consumable product with substitute products (e.g., low-calorie thickeners instead of fats, low-calorie or calorie-free sweeteners instead of conventional sugars). The disadvantage discussed above, according to which the consumer would consume larger amounts of an orally consumable product (particularly a food) having a reduced energy density which in the least favourable case would lead to an increased ingestion of calorically relevant food constituents, is counteracted by using the alkamide or a mixture of alkamides in orally consumable food (particularly food). An alkamide or a mixture of akamides contained in an orally consumable product conveys an early feeling of satiety and at the same time reduces the appetite and the resorption of lipids. In addition it has a positive influence on the consumer's mood, which is a further positive consequence.

Preferably, the orally consumable product according to the invention is selected from the group consisting of sweets, preferably, low-calorie or calorie-free sweets, preferably selected from the group consisting of muesli bar products, fruit gums, coated tablets, hard caramels and chewing gum, Non-alcoholic beverages, preferably selected from the group consisting of green tea, black tea, green or black tea beverages enriched with tea extracts of green tea or black tea, Rooibos tea, other herbal teas, fruit-containing low-sugar or sugar-free lemonades, isotonic beverages, nectars, fruit juices, vegetable juices, fruit juice and vegetable juice compositions, Instant beverages, preferably selected from the group consisting of instant green tea, black tea, Rooibos tea, herbal tea beverages, Cereal products, preferably selected from the group consisting of low-sugar and sugar-free breakfast cereals and muesli bars, Dairy products, preferably selected from the group consisting of low-fat and fat-free dairy beverages, yoghurt, kefir, whey, buttermilk and ice cream, Products made from soy protein or other soy bean fractions, preferably selected from the group consisting of soy milk, products made from soy milk, beverages containing isolated or enzymatically treated soy protein, beverages containing soy flour, compositions containing soy lecithin, products made from compositions containing soy lecithin and mixtures with fruit compositions and optionally flavouring substances.

Sweetener compositions, sweetener tablets and sweetener sachets

Sugar-free coated tablets,

Ice cream with or without constituents on the basis of milk, preferably sugar-free.

Preferably, an orally consumable product according to the invention contains one, two or more sweeteners and/or one, two or more thickeners.

(i) Sweeteners. The term "sweeteners" in this context means substances having a relative sweetening power of at least 25, based on the sweetening power of saccharose (which thus has a sweetening power of 1). Preferably, sweeteners to be used in an orally consumable according to the invention (particularly food, feed or pharmaceutical products) (a) are non-cariogenic and/or have an energy content of a maximum of 5 kcal per gram of the orally consumable product. Advantageous sweeteners in a preferred orally consumable product according to the invention are selected from the following groups (a1) and (a2):

(a1) naturally occuring sweeteners, preferably selected from the group consisting of (a1-1) miraculin, monellin, mabinlin, thaumatin, curculin, brazzein, pentaidin, D-phenylalanine, D-tryptophan, and extracts or fractions obtained from natural sources, containing said amino acids and/or proteins and the physiologically tolerable salts of said amino acids and/or proteins, particularly the sodium, potassium, calcium or ammonium salts;

(a1-2) Neohesperidin-dihydrochalcone, naringin-dihydrochalvone, steviosid, steviolbioside, rebaudiosides, particularly rebaudioside A, rebaudioside B, rebaudioside C, rebaudioside D, rebaudioside E, rebaudioside F, rebaudioside G, rebaudioside H, dulcosides and rubusosides, suavioside A, suavioside B, suavioside G, suavioside H, suavioside I, suavioside J, baiyunoside 1, baiyunoside 2, phlomisoside 1, phlomisoside 2, phlomisoside 3, phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartine, telosmoside A15, periandrin 1-V, pterocaryoside, cyclocaryoside, mukurozioside, trans-anethol, transcinnamaldehyde, bryoside, bryonoside, bryonodulcoside, carnosifloside, scandenoside, gypenoside, trilobtain, phloridzin, dihydroflavanol, hematoxylin, cyarun, chlorogenic acid, albiziasaponin, telosmoside, gaudichaudioside, mogroside, mogroside V, hernandulcine, monatin, phyllodulcin, glycyrrhetin acid and derivatives thereof (for example their glycosides such as glycyrrhizin) and their physiologically tolerated salts such as, particularly, their sodium, potassium, calcium or ammonium salts;

(a1-3) Extracts or enriched fractions of the extracts, selected from the group consisting of *Thaumatococcus* extracts (sweet prayers plant), extracts of *Stevia* ssp. (in particular *Stevia rebaudiana*), swingle extract (*Momordica* or *Siratia grosvenorii*, luo-han-guo), extracts of *Glycerrhyzia* ssp. (in particular *Glycerrhyzia glabra*), *Rubus* ssp. (in particular *Rubus suavissimus*), citrus extracts, extracts of *Lippia dulcis;*

(a2) synthetic sweet tasting substances, preferably selected from the group consisting of magap, sodium cyclamate or other physiologically tolerable salts of cyclamic acid, acesulfame K or other physiologically tolerable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

(ii) Thickeners. Advantageous thickeners in a preferred orally consumable product according to the invention (particularly food, feed or pharmaceutical products) are selected from the group consisting of: crosslinked polyacrylic acids and the derivatives thereof, polysaccharides and the derivatives thereof such as xanthan gum, agar-agar, alginates or tyloses, cellulose derivatives, e.g., carboxymethyl cellulose or hydroxycarboxy-methylcellulose, fatty alcohols, monoglycerides and fatty acids, polyvinyl alcohol and polyvinylpyrrolidone.

Preferable according to the invention is an orally consumable product (particularly food or feed), containing milk and/or cream soured by lactobacillii is preferably selected from the group consisting of orally consumable products with a fat content of 4.0% by weight or less, preferably of 1.5% by weight or less, particularly preferably 0.5% by weight or less, each based on the total weight of the orally consumable product, and/or selected from the group consisting of yoghurt, kefir and quark.

Preferably, the orally consumable product according to the invention (particularly food or feed) which contains milk and/or cream soured by lactobacillii, has an energy content of not more than 150 kcal/100 g of the orally consumable product, preferably not more than 100 kcal/100 g, particularly preferably not more than 75 kcal/100 g, especially preferably not more than 50 kcal/100 g.

A preferred orally consumable product according to the invention (particularly food or feed), which contains milk and/or cream soured by lactobacillii, additionally comprises fruit and/or fruit compositions.

Particularly preferred is an orally consumable product according to the invention, which contains milk and/or cream soured by lactobacillii, wherein the orally consumable product contains (i) sugar and/or (ii) thickeners and/or (iii) gelling agents and/or (iv) sweeteners and/or (v) flavouring substances and/or (vi) preservatives.

"Sugar" within the scope of the present text (unless indicated otherwise or to be understood otherwise from the context) means the collective term for all sweet tasting saccharides (mono- and disaccharides).

Advantageously, an orally consumable product according to the invention (particularly food or feed), which contains milk and/or cream soured by lactobacilli is an orally consumable product containing a probiotic, whereby said probiotic is preferably selected from the group consisting of *Bifidobacterium* animal's subsp. *lactis* BB-12, *Bifidobacterium animalis* subsp. *lactis* DN-173 010, *Bifidobacterium animalis* subsp. *lactis* HNO19, *Lactobacillus acidophilus* LA5, *Lactobacillus acidophilus* NCFM, *Lactobacillus johnsonii* Lal, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

D. Chewing Gums

Particularly preferred is an orally consumable product according to the invention, which is a chewing gum containing a chewing gum base. The chewing gum base in this context is preferably selected from the group consisting of "chewing gum"- or "bubble gum"-bases. The latter are softer, allowing the formation of chewing gum bubbles. Preferred chewing gum bases according to the invention comprise—besides conventionally used natural resins or the natural rubber chicle—elastomers such as polyvinyl acetates (PVA), polyethylens, (low or medium molecular) polyisobutenes (PIB), polybutadienes, Isobutene Isoprene copolymers (butyl rubber), polyvinyl ethyl ethers (PVE), polyvinyl butyl ethers, copolymers of vinyl esters and vinyl ethers, styrene-butadiene copolymers (styrene-butadiene rubber, SBR) or vinyl elastomers, e.g., on the basis of vinyl acetate/vinyl laurate, vinyl acetate/vinyl stearate or ethylene/vinyl acetate, as well as mixtures of the elastomers mentioned such as, for example, described in EP 0 242 325, U.S. Pat. No. 4,518,615, U.S. Pat. No. 5,093,136, U.S. Pat. No. 5,266,336, U.S. Pat. No. 5,601,858 or U.S. Pat. No. 6,986,709. Besides this, preferably used chewing gum bases according to the invention preferably comprise further constituents such as, for example, (mineral) fillers, softeners, emulsifiers, antioxidants, waxes, fats or oils such as, for example, hydrated vegetable or animal fats, mono-, di- or triglycerides. Suitable (mineral) fillers are, for example, calcium carbonate, titanium dioxide, silicon dioxide, talcum, aluminium oxide, dicalcium phosphate, tricalcium phosphate, magnesium hydroxide and mixtures thereof. Suitable softeners or detackifiers are, for example, lanolin, stearic acid, sodium stearate, ethyl acetate, diacetin (glycerine diacetate), triacetine (glycerine triacetate), triethyl citrate. Suitable waxes are, for example, paraffin waxes, candelilla wax, microcrystalline waxes and polyethylene waxes. Suitable emulsifiers are, for example, phosphatides such as lecithin, mono- and diglycerides of fatty acids, e.g., glycerol monostearate.

Chewing gums according to the invention (particularly as disclosed above) preferably comprise constituents such as sugars of different types, sugar substitutes, other sweet tasting substances, sugar alcohols (particularly sorbitol, xylitol, mannitol), cooling agents, flavour correcting agents for unpleasant taste impressions, other taste-modulating substances (for example inositol phosphate, nucleotides such as guanosine monophosphate, adenosine monophosphate or other substances, such as sodium glutamate or 2-phenoxypropionic acid), wetting agents, thickeners, emulsifiers, stabilizers, odour correcting agents and flavouring substances (e.g.: eucalyptus-menthol, cherry, strawberry, grapefruit, vanilla, banana, citrus, peach, black currant, tropical fruit, ginger, coffee, cinnamon, combinations (of the flavouring substances mentioned) with mint flavourings and spearmint and peppermint alone). Particularly interesting is, among others, the combination of the flavourings with further substances having a cooling, warming and/or mouthwatering properties.

E. Beverages

In another preferred form of embodiment of the invention the orally consumable product is a beverage, preferably having a sugar content of 30 g/100 mL beverage or less, preferably of 15 g/100 mL or less, particularly preferably 5 g/100 mL or less, particularly preferably no sugar, and/or wherein the beverage does not contain any ethanol or 0.1 volume percent of ethanol as a maximum based on the volume of the beverage.

Within the scope of the present invention orally consumable products according to the invention are less preferred which are ethanol-containing beverages.

No ethanol means in the present invention that no ethanol is added and that the composition contains less than 0.1 Vol.-%, preferably less than 0.01 Vol.-% and particularly preferably no measurable amount of ethanol.

Particularly preferred are orally consumable products according to the invention (preferably food, feed or pharmaceutical products), wherein they are a carbonated beverage or an uncarbonated beverage.

INDUSTRIAL APPLICATION

Further subject matters of the present invention relate to one or more non-therapeutic methods
  To reduce appetite, particularly also to reduce weight,
  To create a feeling of satiety,
  To reduce caloric resorption, particularly to reduce the uptake and accumulation of lipids and triglycerides and/or
  To enhance the mood Wherein a human or animal being is orally administered a composition containing an effective amount of at least one alkamide.

A further subject matter of the invention is the use of alkamides as means that are orally ingested
  To reduce appetite, particularly also to reduce weight,
  To create a feeling of satiety,
  To reduce caloric resorption, particularly also to reduce the uptake and accumulation of lipids and triglycerides and/or
  To enhance the mood.

With regard to the preferred forms of embodiment, the forms of embodiment already comprehensively described above are incorporated herein by reference, therefore, any repetitions, particularly with regard to preferred alkamides and their required quantities are obsolete.

EXAMPLES

Cell Model

The cell model used for the release of the neurotransmitters dopamine and serotonin are human neuroblastoma cells (SH-SY5Y, ATCC Number CRL-2266). Cultivation is performed at 37° C. and with a 5% $CO_2$ content using a mixture containing at equal parts Eagle's Minimum Essential Medium (MEM) and F12 Medium (each having 10% FBS and 1% Penicillin/Streptomycin). To measure the release of dopamine and serotonin, the cells are harvested with trypsin and seeded, after a vitality check using trypan blue tests, in a defined cell number in 35 mm cell culture dishes.

The cell model used for short-term uptake of free fatty acids and long-term lipid accumulation in the adipocytes are murine fibroblasts (3T3-L1, ATTC Number CL-173) after the cells differentiated to form adipocytes. 3T3-L1 fibroblasts are cultivated at 37° C. and a 5% $CO_2$ content with Dulbecco's Modified Eagle Medium (DMEM) having 10% FBS, 4% L-Glutamin and 1% Penicillin/Streptomycin (=basal medium). Adipocyte differentiation occurs two days after reaching confluence by adding 10 µg/L Insulin, 1 µM dexamethasone and 0.5 mM Isobutylmethylxanthin into the culture medium (=differentiation medium). After two days of cultivation in differentiation medium the adipocytes are allowed to mature for two further days by adding 10 µg/L insulin into the culture medium (=maturation medium). After having spent between three and five days in basal medium, the adipocytes are optimally differentiated and show by inclusion of lipid droplets the phenotype that is typical for adipocytes. Human colon cell line CaCo-2 (ATCC Number HTB-37) is used as a cell model for the uptake of free fatty acids by the small intestine after they have differentiated to form a phenotype corresponding to enterocytes. CaCo-2 cells are cultivated at 37° C. with a 5% $CO_2$ content with Dulbecco's Modified Eagle Medium (DMEM) with 10% FBS, 2% L-glutamin and 1% penicillin/streptomycin. Enterocyte differentiation is performed by cultivating the cells in a period of 18 days after they reach confluence.

Example 1

Release of Serotonin in an Experimental Cell System Including Alkamides

After a 3-minute stimulation of $1.25*10^6$ human neuroblastoma cells (SH-SY5Y) with 300 µL Krebs-Ringer-HEPES buffer, 0.1% ascorbic acid, pH 6.2, with, or without, the addition of an alkamide (trans-Pellitorine, dihydropellitorine, spilanthol, wherein when adding the alkamide in concentrations of 0.001 µM, 0.1 µM 1 µM and 10 µM within the Krebs-Ringer-HEPES buffer is adjusted), the serotonin content is detected by means of an enzyme-based method of detection (Serotonin-ELISA sensitive, DLD Diagnostica, Hamburg, Germany). The cells are lysed with a buffer containing sodium lauryl sarcosinate and the DNA content is detected by means of a NanoQuant plate (Tecan, Ménnendorf, Switzerland) to normalize serotonin release.

Table 1 represents the influence of trans-pellitorine on serotonin release in SH-SY5Y cells. A concentration of 100 nM t-pellitorine increases the release of serotonin by 40%.

Figure 1A:
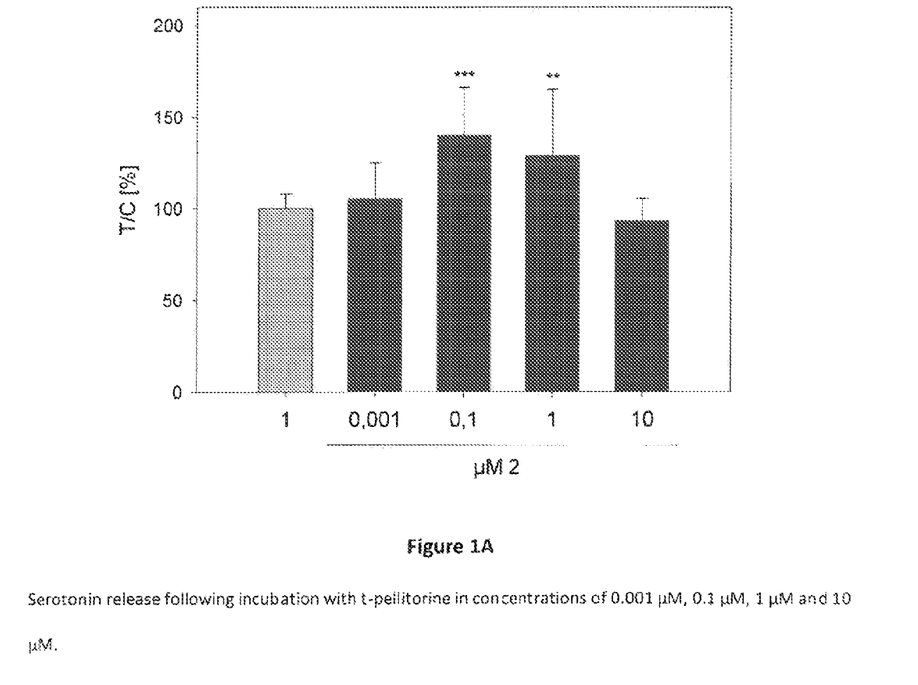
FIG. 1A is a graph illustrating serotonin release following incubation with t-pellitorine (2)
Figure 1B:
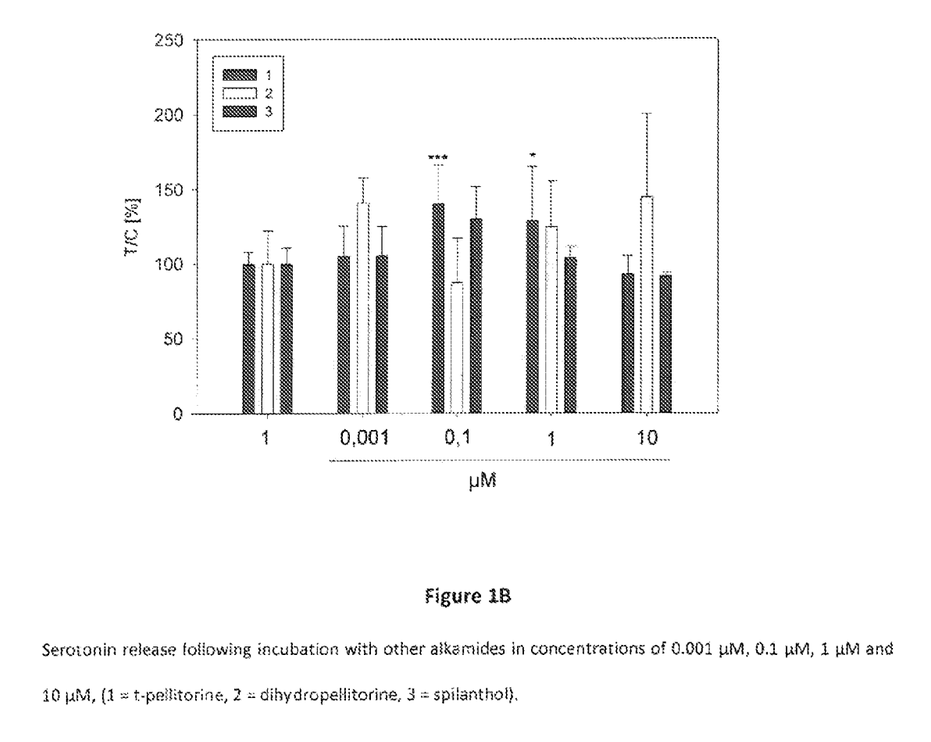
FIG. 1B is a graph illustrating serotonin release following incubation with other alkamides.

FIGS. 1a and 1b represent the release of serotonin after incubation with t-pellitorine (2) (FIG. 1A) in concentrations of 0.001 µM, 0.1 µM, 1 µM and 10 µM or other alkamides (FIG. 1B: 1=t-pellitorine, 2=dihydropellitorine, 3=spilanthol)). Results are represented in % relative to control (buffer with 0.1% ethanol) n=3, tR=2. Significant differences of control treatment were tested using a one-way ANOVA with a subsequent Holm-Sidak post hoc test and marked according to the following pattern: *$p \leq 0.05$; $p. \leq 0.01$; *$p \leq 0.001$.

TABLE 1

Serotonin release SH-SY5Y cells after stimulation with different alkamide concentrations

| Test substance | T/C [%] | Standard error [%] |
| --- | --- | --- |
| EtOH control (t-pellitorine) | 100.0 | 7.93 |
| trans-pellitorine 0.001 µM | 105.3 | 19.9 |
| trans-pellitorine 0.1 µM | 140.2 | 25.9 |
| trans-pellitorine 1 µM | 128.8 | 36.1 |
| trans-pellitorine, 10 µM | 93.02 | 12.7 |
| EtOH control (dihydropellitorine) | 100.0 | 22.2 |
| Dihydropellitorine 0.001 µM | 140.9 | 16.7 |
| Dihydropellitorine 0.1 µM | 87.41 | 29.5 |
| Dihydropellitorine 1 µM | 124.3 | 31.1 |
| Dihydropellitorine 10 µM | 144.5 | 55.8 |
| EtOH control (spilanthol) | 100.0 | 10.5 |
| Spilanthol 0.001 µM | 105.6 | 19.3 |
| Spilanthol 0.1 µM | 129.9 | 21.7 |
| Spilanthol 1 µM | 103.8 | 7.62 |
| Spilanthol 10 µM | 91.77 | 2.24 |

Example 2

Release of Dopamine in an Experimental Cell System Using Trans-Pellitorine

Method for Measuring the Release of Dopamine:

After a 3-minute stimulation of $1.25*10^6$ of human neuroblastoma cells (SH-SY5Y) with 350 µL Krebs-Ringer-HEPES Puffer (1), pH 5, with or without the addition of trans-pellitorine (2) in concentrations of 0.001 µM, 0.1 µM, 1 µM and 10 µM the supernatant is acidified with 1 N HCl and the dopamine content is determined by means of an enzyme-based method of detection (Dopamin-ELISA, DLD Diagnostica, Hamburg, Germany). The cells are lysed with a buffer containing sodium lauryl sarcosinate and the DNAN content is determined by means of a NanoQuant plant (Tecan, Ménnendorf, Switzerland) for normalization of dopamine release. During an ethanol control (EtOH control) no trans-pellitorine is added to the Krebs-Ringer-HEPES buffer, but ethanol is added to the buffer such that a 0.1% ethanolic Krebs-Ringer-HEPES buffer solution is obtained.

Table 2 represents the dopamine release by SH-SY5Y cells after stimulation with different concentrations of the alkamide t-pellitorine.

Figure 2:
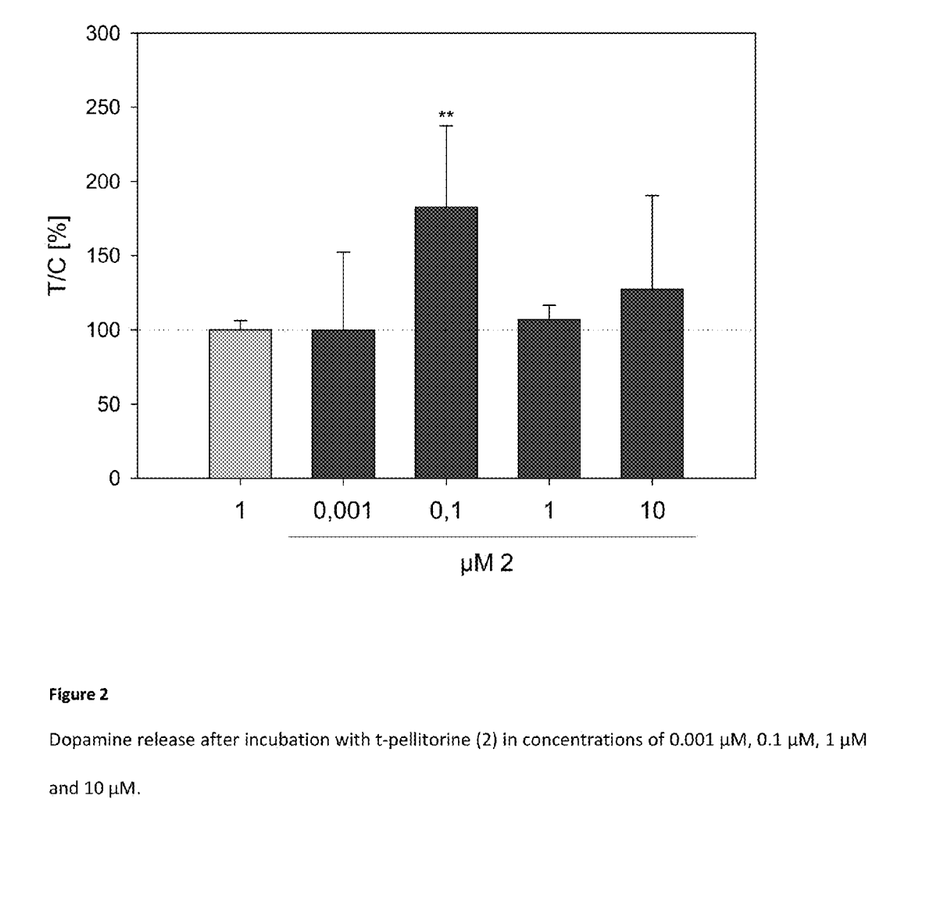
FIG. 2 is a graph illustrating dopamine release after incubation with t-pellitorine (2)

FIG. 2 represents the release of dopamin after incubation with t-pellitorine (2) in concentrations of 0.001 µM, 0.1 µM, 1 µM and 10 µM. The results are represented in a control-to-case ratio expressed in percent (buffer with 0.1% ethanol). n=3, tR=2. Significant differences between the treatments and control were tested using a one-way ANOVA with a subsequent Holm-Sidak post hoc test and marked according to the following pattern: *$p \leq 0.05$; $p \leq 0.01$; *$p \leq 0.001$.

TABLE 2

Dopamine release by SH-SY5Y cells following stimulation with different concentrations of the alkamide t-pellitorine.

| Test substance | T/C [%] | Standard error [%] |
| --- | --- | --- |
| EtOH control | 100.0 | 6.22 |
| trans-pellitorine 0.001 µM | 99.68 | 52.61 |
| trans-pellitorine 0.1 µM | 182.7 | 54.78 |
| trans-pellitorine 1 µM | 106.8 | 9.877 |
| trans-pellitorine 10 µM | 127.3 | 63.15 |

Table 2 and FIG. 2 show the strong influence of low concentrations of trans-pellitorine on the release of dopamine. Already a concentration of 100 nM of trans-pellitorine leads to an increase of 80% of dopamine release by SH-SY5Y cells.

Example 3

Reduction of Fatty Acid Uptake in 3T3-L1 Cells

Method of Determining Fatty Acid Uptake in 3T3-L1 Cells:

After differentiation of 3T3-L1 fibroblasts to form adipocytes, 65000 cells per well are seeded in a 96 well plate and incubated at 37° C. for four hours with basal medium (DMEM+10% fetal bovine serum) and then incubated for an hour with serum-free medium. The cells were pre-treated with 0.1 µM, 1 µM and 10 µM t-pellitorine for 30 minutes. The uptake of free fatty acids into the cells was measured by means of the fluorescence-marked fatty acid BODIPY® (QBT Fatty Acid Uptake Corporation, Germany) with a fluorescence microplate reading device (Tecan, Ménnendorf, Switzerland) every 20 seconds for a period of 60 minutes.

Table 3 represents the fatty acid uptake by 3T3-L1 cells after stimulation with different concentrations of the alkamide t-pellitorine.

Figure 3:
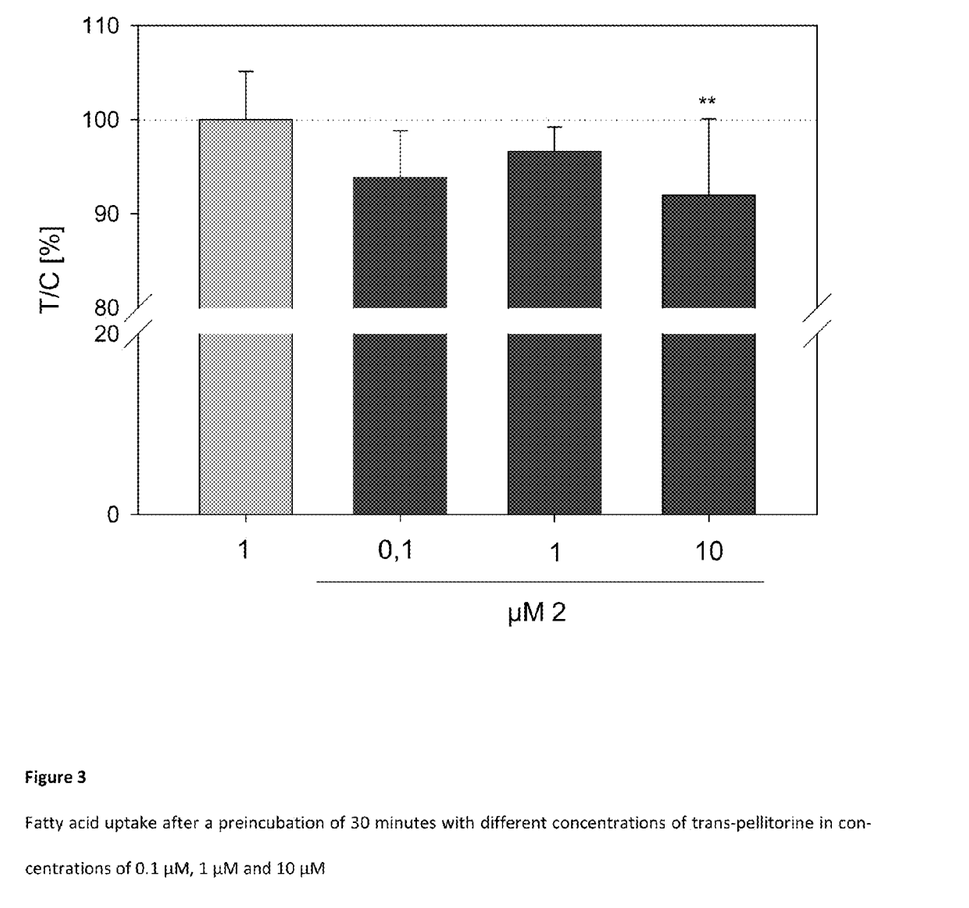
FIG. 3 is a graph illustrating fatty acid uptake after preincubation with different concentrations of trans-pellitorine.

FIG. 3 shows the fatty acid uptake after a preincubation of 30 minutes with different concentrations of trans-pellitorine in concentrations of 0.1 µM, 1 µM and 10 µM. The results are represented as an area below the curve after measuring of 60 minutes in comparison with control (1, buffer with 0.1% Ethanol). n=3, tR=2-3. Significant differences between the treatment and control were tested by means of an one-way ANOVA followed by a Holm-Sidak post hoc test and marked according to the following pattern: *$p \leq 0.05$; $p \leq 0.01$; *$p \leq 0.001$

TABLE 3

Fatty acid uptake by 3T3-L1 cells following stimulation with different concentrations of the alkamide t-pellitorine

| Test substance | T/C [%] | Standard error [%] |
| --- | --- | --- |
| Ethanol control | 100.0 | 5.12 |
| trans-pellitorine 0.1 µM | 93.84 | 4.97 |
| trans-pellitorine 1 µM | 96.63 | 2.58 |
| trans-pellitorine 10 µM | 91.95 | 8.12 |

The present data show that a preincubation with 10 µM t-pellitorine results in a reduction of fatty acid uptake by 9% in adipocytes.

Example 4

Reduction of Long Time Lipid Accumulation in 3T3-L1 Cells

Method of Determining Long Time Lipid Accumulation in 3T3-L1 Cells:

After differentiation of the 3T3-L1 fibroblasts to form adipocytes the cells are treated for 10 days with trans-pellitorine in concentrations of 0.001 µM, µM 0.1 µM, 1 µM and 10 µM and a final concentration of 10 µg/L insulin. The cells were then fixed with a 10% solution of paraformaldehyde and the intracellular lipid droplets were coloured with a 2.1% Oil-Red 0 solution in a mixture of isopropanol/water (60/40). Residual colouring was removed by washing with double distilled water. The dye Oil-Red 0 is subsequently removed by means of 100% isopropanol, and absorption of the Oil-Red 0 solution, which behaves proportionally to the lipid droplets of the cells, was determined by means of a microplate reading device (Tecan, Ménnendorf, Switzerland).

Table 4 represents the lipid accumulation in 3T3-L1 cells after stimulation with different concentrations of the alkamide t-pellitorine.

Figure 4:
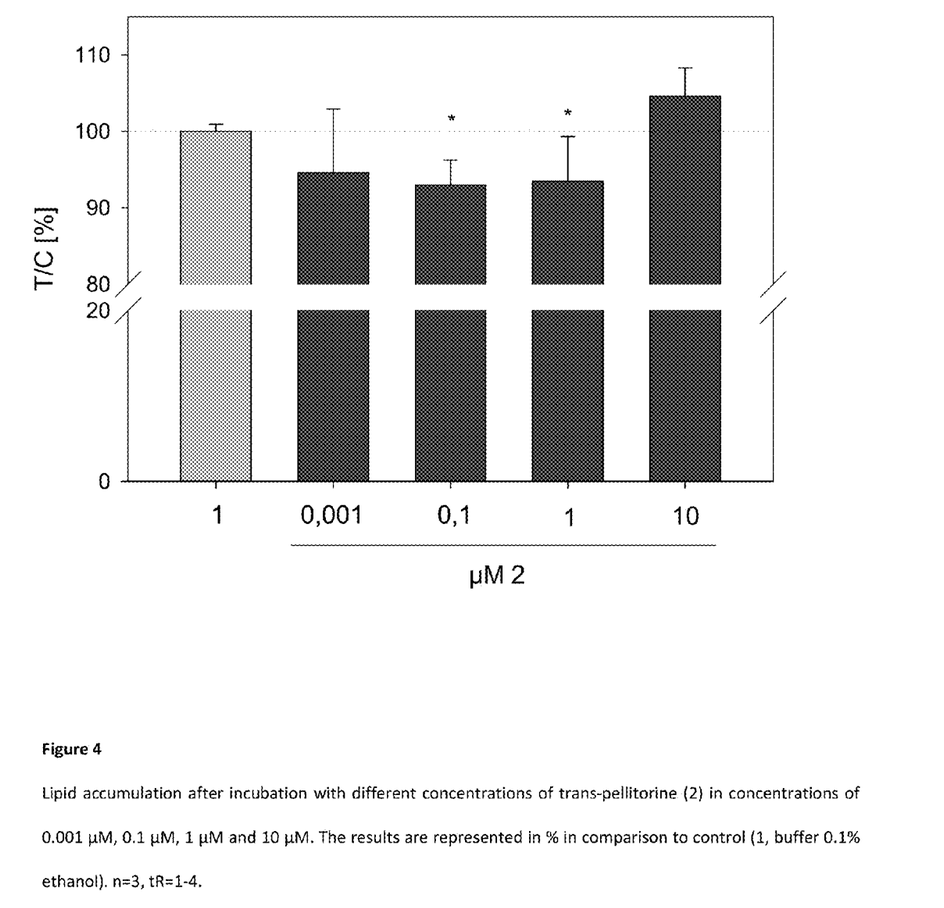
FIG. 4 is a graph illustrating lipid accumulation after incubation with different concentrations of trans-pellitorine (2)

FIG. 4 shows the lipid accumulation after incubation with different concentrations of trans-pellitorine (2) in concentrations of 0.001 µM, 0.1 µM, 1 µM and 10 µM. The results are indicated in % in comparison to control (1, buffer 0.1% ethanol). n=3, tR=1-4. Significant differences between the treatment and control were tested by means of a one-way ANOVA followed by a Holm-Sidak post hoc test and marked according to the following pattern: *p≤0.05; p≤0.01; *p≤0.001

TABLE 4

Lipid accumulation in 3T3-L1 cells following stimulation with different concentrations of the alkamide t-pellitorine.

| Test substance | T/C [%] | Standard error [%] |
|---|---|---|
| Ethanol control | 100.0 | 0.93 |
| trans-pellitorine 0.001 µM | 94.60 | 8.32 |
| trans-pellitorine 0.1 µM | 92.94 | 3.28 |
| trans-pellitorine 1 µM | 93.46 | 5.86 |

Example 5

Reduction of Fatty Acid Uptake in Differentiated CaCo-2 Cells

After differentiation of the CaCo-2 cells to form an enterocyte phenotype, the cells are incubated with serum-free medium for an hour. Subsequently the cells are pre-treated with 0.1 µM, 1 µM and 10 µM t-pellitorine for 30 minutes and the free fatty acid uptake into the cells was measured by means of the fluorescence marked fatty acid BODIPY® (QBT Fatty Acid Up-take Corporation, Germany) at a fluorescence microplate reading device (Tecan, Ménnendorf, Switzerland) every 20 seconds for a period of 60 minutes.

Table 5 represents the fatty acid uptake in differentiated CaCo-2 following stimulation with different concentrations of the alkamide t-pellitorine.

Figure 5:
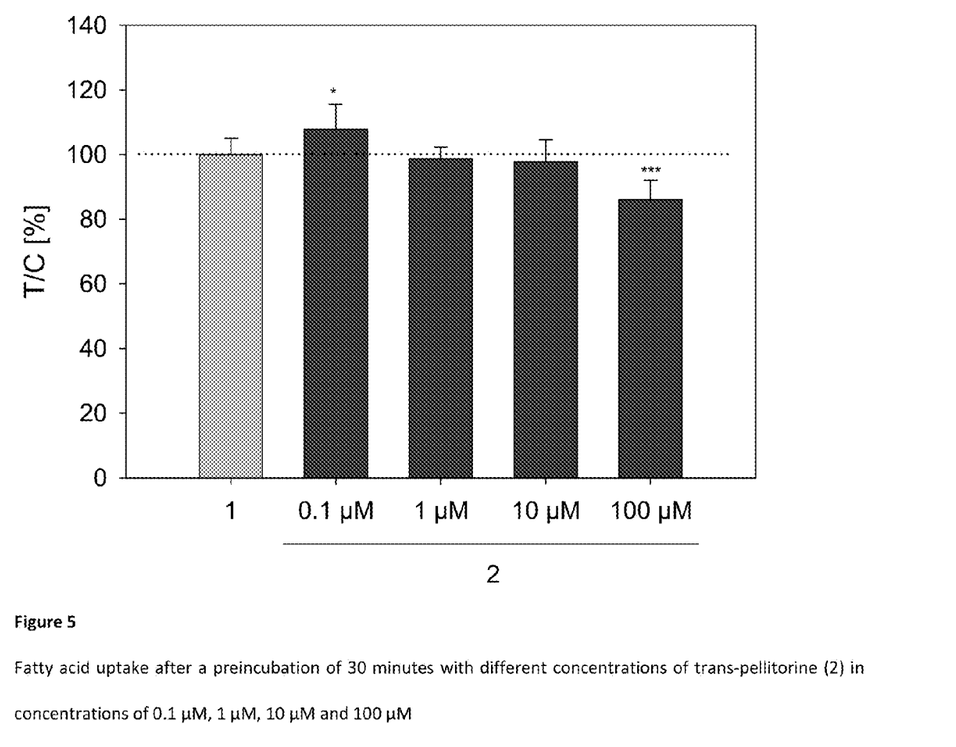
FIG. 5 is a graph illustrating fatty acid uptake following preincubation with different concentrations of trans-pellitorine (2).

FIG. 5 shows the fatty acid uptake following a preincubation of 30 minutes with different concentrations of trans-pellitorine (2) in concentrations of 0.1 µM, 1 µM, 10 µM and 100 µM. The results are represented as an area below the curve after measuring for 60 minutes in comparison to control (1, buffer with 0.1% ethanol). n=3, tR=2-3. Significant differences between the treatment and control were tested by means of a one-way ANOVA followed by a Holm-Sidak post hoc test and marked according to the following pattern: *p≤0.05; p.≤0.01; *p≤0.001

TABLE 5

Fatty acid uptake in differentiated CaCo-2 following stimulation with different concentrations of the alkamide t-pellitorine.

| Test substance | T/C [%] | Standard error [%] |
|---|---|---|
| Ethanol control | 100.0 | 5.01 |
| trans-pellitorine 0.1 µM | 107.8 | 7.84 |
| trans-pellitorine 1 µM | 98.7 | 3.58 |
| trans-pellitorine 10 µM | 97.8 | 6.81 |
| trans-pellitorine 100 µM | 86.0 | 6.05 |

The present data show that a preincubation with 100 µM t-pellitorine of 30 minutes results in a reduction of free fatty acid uptake by 14% in an enterocyte model.

Examples of Use

The present invention is in the following explained in more detail by examples of use. All indications of quantity will be understood to mean % by weight if not indicated otherwise.

TABLE I

| | Soft drinks (sugar-containing, low-calorie, calorie-free) | | | | | | |
|---|---|---|---|---|---|---|---|
| Ingredient | A | B | C | D | E | F | G |
| Sugar (sucrose) | 10 | 10 | 7 | — | — | 8 | 7 |
| Glucose/fructose syrup from maize, containg 55 % by weight fructose | — | — | — | — | 10 | — | — |
| Rebaudioside A 95% | — | — | 0.02 | 0.05 | — | — | — |
| Citric acid | 0.15 | 0.15 | 0.06 | 0.15 | 0.15 | 0.15 | 0.15 |
| Phosphoric acid | — | — | 0.07 | — | — | — | — |
| Colouring caramel | — | — | 0.14 | — | — | — | — |
| Caffeine | — | — | 0.01 | — | — | — | — |
| Lemon flavouring | 0.1 | 0.05 | — | 0.1 | 0.1 | 0.1 | 0.1 |
| Lime flavouring | — | 0.05 | — | — | — | — | — |
| Beverage emulsion Type "Cola" | — | — | 0.05 | — | — | — | — |
| Phloretin | — | — | 0.002 | 0.003 | — | 0.002 | 0.001 |
| Hesperetin | — | — | 0.001 | 0.002 | — | — | 0.002 |
| Extract of *Rubus suavisimus*, containing 5% by weight rubusoside based on the total weight of the extract | — | — | — | — | — | 0.01 | — |

TABLE I-continued

Soft drinks (sugar-containing, low-calorie, calorie-free)

| Ingredient | A | B | C | D | E | F | G |
|---|---|---|---|---|---|---|---|
| Homoeriodictyol sodium salt | — | — | 0.005 | 0.005 | — | — | — |
| trans-pellitorine | 0.000002 | 0.00005 | — | 0.00001 | 0.000001 | 0.0001 | 0.00005 |
| Spilanthol | — | 0.00005 | 0.00005 | — | 0.000001 | — | — |
| Water | | | | Ad 100 | | | |

The ingredients were mixed in the indicated order and filled up with water to 100%. The mixtures were filled into glass bottles and carbonized.

TABLE II

Use in a chewing gum

| Component | Ingredient | A | B |
|---|---|---|---|
| A | Chewing gum base, Company "Jagum T" | 30.4899 | 30.49999 |
| B | Sorbitol, pulverized | 39.00 | 39.00 |
|   | Isomalt ® (Palatinit GmbH) | 9.50 | 9.50 |
|   | Xylit | 2.00 | 2.00 |
|   | Mannit | 3.00 | 3.00 |
|   | Aspartam ® | 0.10 | 0.10 |
|   | Acesulfam ® K | 0.10 | 0.10 |
|   | Emulgum ® (Colloides Naturels, Inc.) | 0.30 | 0.30 |
| C | Sorbitol, 70% | 14.00 | 14.00 |
|   | Glycerol | 1.00 | 1.00 |
| D | Peppermint flavouring | 0.5 | 0.5 |
|   | trans-pellitorine | 0.00002 | 0.0002 |
|   | Eriodictyol | 0.0100 | — |

Parts A to D are mixed and intensively kneaded. The raw mass can be processed to chewing gum ready for consumption, e.g., in the form of thin stripes.

TABLE III

Use in hard caramels

| Ingredients | A | B | C | D |
|---|---|---|---|---|
| Sugar | 74.50 | — | — | — |
| Palatinit, Type M | — | 74.00 | 75.50 | 75.00 |
| Citric acid | 0.5 | 1.0 | 0.5 | — |
| Yellow colouring | — | 0.01 | — | — |
| Red colouring | — | — | 0.01 | — |
| Blue colouring | 0.01 | — | — | 0.01 |
| Peppermint flavouring | 0.1 | — | — | 0.1 |
| Lemon flavouring | — | 0.1 | — | — |
| Red fruit flavouring | — | — | 0.1 | — |
| Rebaudioside A 98% | — | 0.040 | — | 0.040 |
| Balansin A according to [SY317] | — | 0.005 | 0.010 | 0.005 |
| Hesperetin | — | 0.001 | — | 0.001 |
| Phloretin | — | 0.002 | — | — |
| trans-pellitorine | 0.0002 | 0.00001 | 0.000002 | 0.0002 |
| Spilanthol | — | 0.00001 | — | — |
| Water | ad 100 | ad 100 | ad 100 | ad 100 |

Palatinit or sugar, optionally after adding citric acid, was mixed with water and the mixture was melted at 165° C. and then cooled to 115° C. Flavouring and other constituents were added and, after mixing, moulded and removed from the moulds after solidifying and then individually wrapped.

TABLE IV

Low-fat yoghurts

| Ingredients | A | B | C | D |
|---|---|---|---|---|
| Sucrose | 10 | 8 | 6 | — |
| Rebaudioside A 98% | — | — | — | 0.050 |
| Extract of *Rubus suavissimus*, containing 5% by weight rubusoside based on the total weight of the extract, e.g., of plant extract | — | 0.010 | 0.010 | — |
| Hesperetin | — | 0.001 | 0.001 | 0.002 |
| Phloretin | — | — | 0.002 | 0.002 |
| Homoeriodictyol sodium salt | — | — | — | 0.005 |
| trans-pellitorine | 0.00002 | 0.0001 | 0.000002 | 0.0001 |
| yoghurt, 0.1% fat | | Fill up to 100% | | |

The ingredients were mixed and cooled down to 5° C.

TABLE V

Fruit gums

| Ingredients | A | B |
|---|---|---|
| Saccharose | 34.50 | 8.20 |
| Glucose syrup, DE 40 | 31.89 | 30.09 |
| Iso Syrup C* Tru Sweet 01750 (Cerestar GmbH) | 1.50 | 2.10 |
| Gelatin 240 Bloom | 8.20 | 9.40 |
| Polydextrose (Litesse ® Ultra, Danisco Cultor GmbH) | — | 24.40 |
| Yellow and red colouring | 0.01 | 0.01 |
| Citric acid | 0.20 | — |
| Cherry flavour, containing 1% by weight hesperetin 2 and 0.3% by weight phloretin based on the flavouring | — | 0.10 |
| trans-pellitorine | 0.0002 | 0.00002 |
| Spilanthol | 0.00001 | — |
| Water | ad 100 | ad 100 |

Polydextrose is a non-sweet tasting polysaccharide with a low calorific value.

The invention claimed is:

1. A non-therapeutic process for the reduction of appetite and/or creation of a feeling of satiety and/or to reduce calorie resorption comprising: orally administering a composition comprising in an amount of from 0.002 mg/kg to 0.20 mg/kg at least one alkamide selected from the group consisting of 2E,4E-decadienic acid-N-isobutylamide (trans-pellitorine); 2E,4Z-decadienic acid-N-isobutylamide (cis-pellitorine); 2Z,4Z-decadienic acid-N-isobutylamide; 2Z,4E-decadienic acid-N-isobutylamide, 2E,4E-decadienic acid-N-([2S]-2-methylbutyl)amide; 2E,4E-decadienic acid-N-([2S]-2-methylbutyl)amide; 2E,4E-decadienic acid-N-([2R]-2-methylbutylamide); 2E,4Z-decadienic acid-N-(2-methylbutyl)amide;

2E,4E-decadienic acid-N-piperidine (achilleamide); 2E-decenoic acid-N-isobutylamide; 2E,6Z,8E-decatrienoic acid N-isobutylamide (spilanthol); 2E,6Z,8E-decatrienoic acid N-([2S]-2-methylbutyl)amide (homospilanthol); 2E,6Z,8E-decatrienoic acid-N-([2R]-2-methylbutyl)amide; 2E-decen-4-inoic acid-N-isobutyl amide; 2Z-decen-4-inoic acid N-isobutyl amine; 2E,6Z,8E,10E-dodecatetraenoic acid N-(2-methylpropyl)amide (α-sanshool); 2E,6Z,8E,10E-dodecatetraenoic acid N-(2-hydroxy-2-methylpropyl)amide (α-hydroxysanshool); 2E,6E,8E,10E-dodecatetraenoic acid N-(2-hydroxy-2-methylpropyl)amide (β-hydroxysanshool; 2E,4E,8Z,10E,12E-tetradecapentaenoic acid N-(2-hydroxy-2-methylpropyl)amide (γ-hydroxysanshool); 2E,4E,8E,10E,12E-tetradecapentaenoic acid N-(2-hydroxy-2-methylpropyl)amide (γ-hydroxyisosanshool); 2E,4E,8Z,10E,12E-tetradecapentaenoic acid N-(2-methyl-2-propenyl)amide (y-dehydrosanshool); 2E,4E,8Z,10E,12E-tetradecapentaenoic acid N-(2-methylpropyl)amide (y-sanshool); 2E,4E,8Z,11Z-tetradecatetraenoic acid N-(2-hydroxy-2-methylpropyl)amide (bungeanool), 2E,4E,8Z,11E-tetradecatetraenoic acid N-(2-hydroxy-2-methylpropyl)amide (isobungeanool), 2E,4E,8Z-tetradecatrienoic acid N-(2-hydroxy-2-methylpropyl)amide (dihydrobungeanool) and 2E,4E-tetradecadienoic acid N-(2-hydroxy-2-methylpropyl)amide (tetrahydrobungeanool) to a human or an animal in need of appetite reduction or caloric reduction.

2. The process of claim 1, wherein said composition is a food, feed or dietary supplement.

3. The process of claim 1, wherein said composition is present in a spray-dried form.

4. The process of claim 1, wherein said composition is present in encapsulated form.

5. The process of claim 1, wherein said composition further contain sweeteners and/or thickeners.

* * * * *